(12) United States Patent
Keren et al.

(10) Patent No.: US 9,492,196 B2
(45) Date of Patent: Nov. 15, 2016

(54) HAIR IMPLANT ANCHORS AND SYSTEMS AND METHODS FOR USE THEREOF

(75) Inventors: Dvir Keren, Tel Aviv (IL); Boaz Shenhav, Tel Aviv (IL)

(73) Assignee: HAIRSTETICS, LTD., Omer (IL)

( * ) Notice: Subject to any disclaimer, the term of this patent is extended or adjusted under 35 U.S.C. 154(b) by 481 days.

(21) Appl. No.: 13/511,182

(22) PCT Filed: Nov. 24, 2010

(86) PCT No.: PCT/IL2010/000983
§ 371 (c)(1),
(2), (4) Date: May 22, 2012

(87) PCT Pub. No.: WO2011/064772
PCT Pub. Date: Jun. 3, 2011

(65) Prior Publication Data
US 2012/0245612 A1    Sep. 27, 2012

Related U.S. Application Data

(60) Provisional application No. 61/283,045, filed on Nov. 27, 2009.

(51) Int. Cl.
*A61B 17/34* (2006.01)
*A61F 2/10* (2006.01)
(Continued)

(52) U.S. Cl.
CPC ............ *A61B 17/3468* (2013.01); *A61F 2/10* (2013.01); *A61B 2017/00752* (2013.01);
(Continued)

(58) Field of Classification Search
CPC ................... A61F 2/10; A61B 17/3468; A61B 2017/00752; A61B 2017/0409; A61B
(Continued)

(56) References Cited

U.S. PATENT DOCUMENTS 3,003,155 A    10/1961  Mielzynski et al.
3,062,214 A    11/1962  Maxwell
(Continued)

FOREIGN PATENT DOCUMENTS

CN    1192754 C      3/2005
CN    101128156 A    2/2008
(Continued)

OTHER PUBLICATIONS

International Search Report for PCT/IL2010/000983 dated Mar. 15, 2011.
(Continued)

*Primary Examiner* — Corrine McDermott
*Assistant Examiner* — Sarah Simpson
(74) *Attorney, Agent, or Firm* — Finnegan, Henderson, Farabow, Garrett & Dunner, L.L.P.

(57) ABSTRACT

A hair implant anchor usable with a hair implant anchor deployment device for inserting one or more hairs into a tissue portion is provided. The hair implant anchor includes a holder configured to grip one or more hairs and one or more selectably deployable leaves formed with the holder. When the anchor is in its first configuration prior to implantation of the hairs, the leaves are constrained by the deployment device in a position generally parallel to an insertion axis, and in a second configuration, subsequent to implantation of the hair, the leaves adopt a position extended away from the insertion axis, thereby securing the holder and hair gripped thereby within the tissue portion. The invention also provides a method for use of the anchor, a hair implantation system, a multi-hair implantation system and a hair implantation assembly.

26 Claims, 11 Drawing Sheets

(51) Int. Cl.
　　　*A61B 17/00*　　　　(2006.01)
　　　*A61B 17/04*　　　　(2006.01)

(52) U.S. Cl.
　　　CPC ............... *A61B 2017/00867* (2013.01); *A61B 2017/00969* (2013.01); *A61B 2017/0409* (2013.01); *A61B 2017/0412* (2013.01); *A61B 2017/0458* (2013.01)

(58) Field of Classification Search
　　　CPC ............... 2017/0412;A61B 2017/0458; A61B 2017/00969
　　　USPC .......................................... 606/187, 131, 133
　　　See application file for complete search history.

(56) References Cited

U.S. PATENT DOCUMENTS

| | | | |
|---|---|---|---|
| 3,119,398 A | 1/1964 | Bennett et al. | |
| 3,596,292 A | 8/1971 | Erb et al. | |
| 3,699,969 A | 10/1972 | Allen | |
| 3,811,425 A | 5/1974 | Widdifield | |
| 3,858,245 A | 1/1975 | Nate, II et al. | |
| 3,862,453 A | 1/1975 | Widdifield | |
| 3,998,230 A | 12/1976 | Miller | |
| 4,004,592 A | 1/1977 | Yamada | |
| 4,024,315 A | 5/1977 | Yamada | |
| 4,144,876 A | 3/1979 | DeLeo | |
| 4,160,453 A | 7/1979 | Miller | |
| 4,216,777 A | 8/1980 | Pridemore | |
| 4,221,212 A | 9/1980 | Miller | |
| 4,263,913 A | 4/1981 | Malmin | |
| 4,479,291 A | 10/1984 | Yamada | |
| 4,491,134 A | 1/1985 | Malmin | |
| 4,517,997 A | 5/1985 | Forchetti | |
| 4,583,540 A | 4/1986 | Malmin | |
| 4,588,408 A | 5/1986 | Yamada | |
| 4,751,927 A | 6/1988 | Yamada | |
| 4,834,119 A | 5/1989 | Yamada | |
| 4,880,428 A | 11/1989 | Yamada | |
| 4,944,751 A | 7/1990 | Yamada | |
| 4,947,877 A | 8/1990 | Meyer et al. | |
| 4,969,903 A | 11/1990 | Valle | |
| 5,005,596 A | 4/1991 | Yamada | |
| 5,061,284 A | 10/1991 | Laghi | |
| 5,137,533 A | 8/1992 | Giampapa | |
| 5,417,683 A | 5/1995 | Shiao | |
| 5,531,342 A | 7/1996 | Ueda | |
| 5,611,810 A | 3/1997 | Arnold et al. | |
| 5,690,678 A * | 11/1997 | Johnson | 606/232 |
| 5,800,545 A | 9/1998 | Yamada et al. | |
| 5,817,120 A | 10/1998 | Rassman | |
| 5,888,202 A | 3/1999 | Amiri | |
| 5,951,572 A | 9/1999 | Markman | |
| 6,110,189 A | 8/2000 | Markman | |
| 6,461,369 B1 | 10/2002 | Kim | |
| 6,474,344 B2 | 11/2002 | Yamada | |
| 2003/0036770 A1 | 2/2003 | Markman | |
| 2003/0195625 A1 | 10/2003 | Garcia Castro et al. | |
| 2004/0254609 A1 * | 12/2004 | Esplin | 606/232 |
| 2007/0067033 A1 | 3/2007 | Bonati | |
| 2007/0112385 A1 | 5/2007 | Conlon | |

FOREIGN PATENT DOCUMENTS

| | | |
|---|---|---|
| DE | 1953026 | 2/1972 |
| FR | 2715805 A1 | 8/1995 |
| WO | WO 8808286 | 11/1988 |
| WO | WO 2010079928 A2 | 7/2010 |

OTHER PUBLICATIONS

Translation of Search Report from State Intellectual Property of China for corresponding Chinese patent application No. 201080052967.4.

* cited by examiner

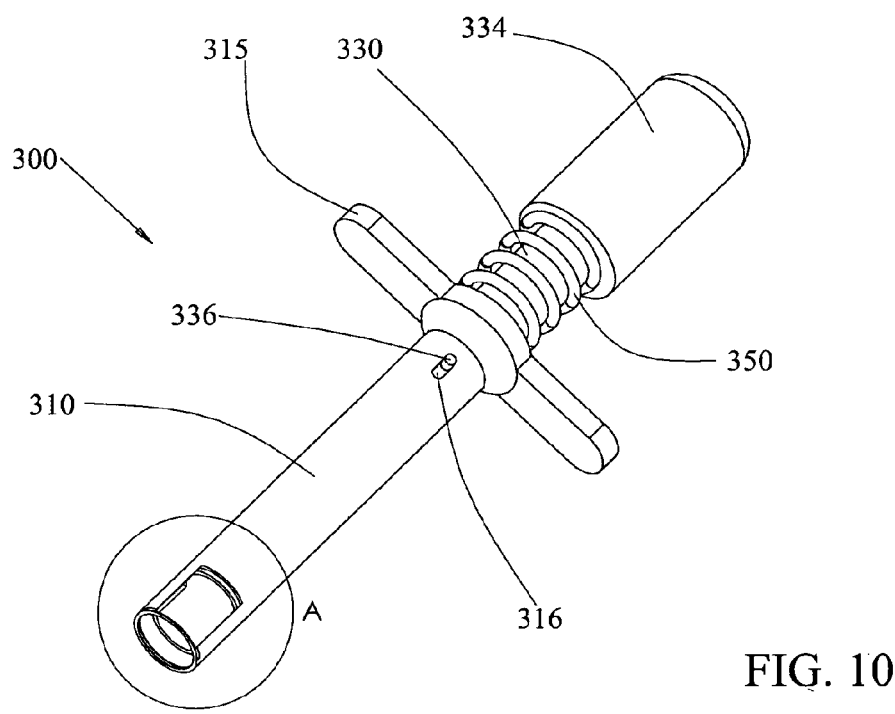
FIG. 10
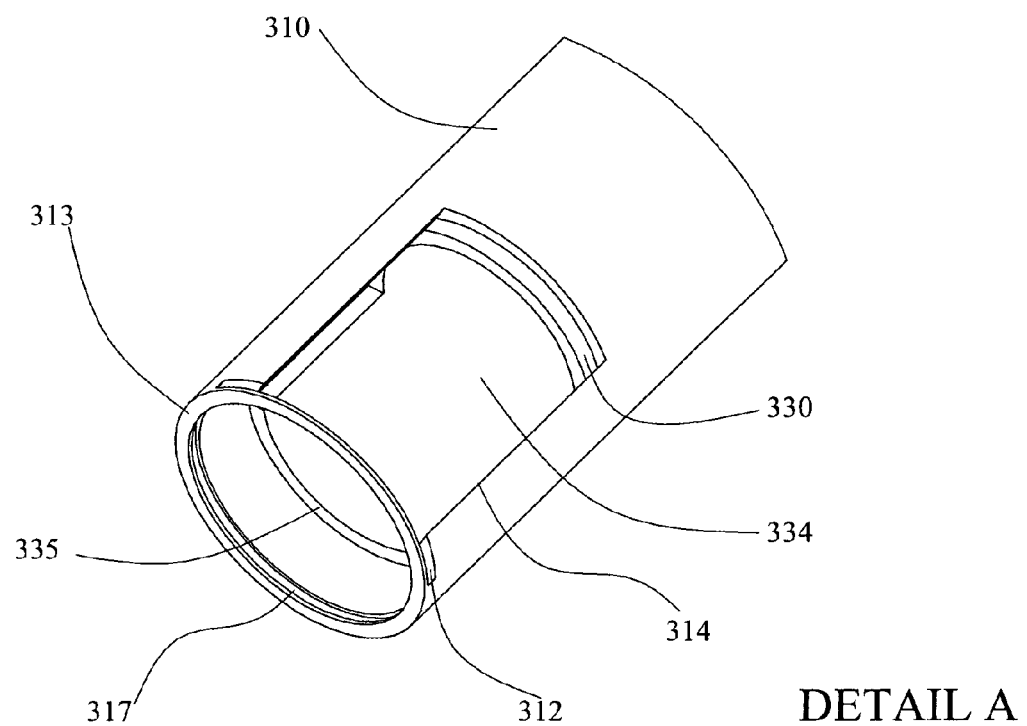
DETAIL A

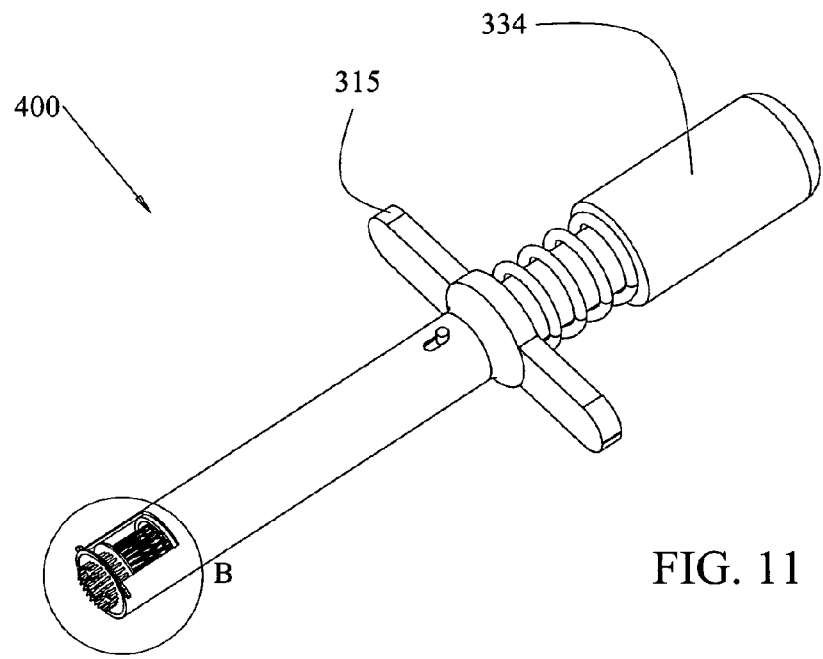
FIG. 11
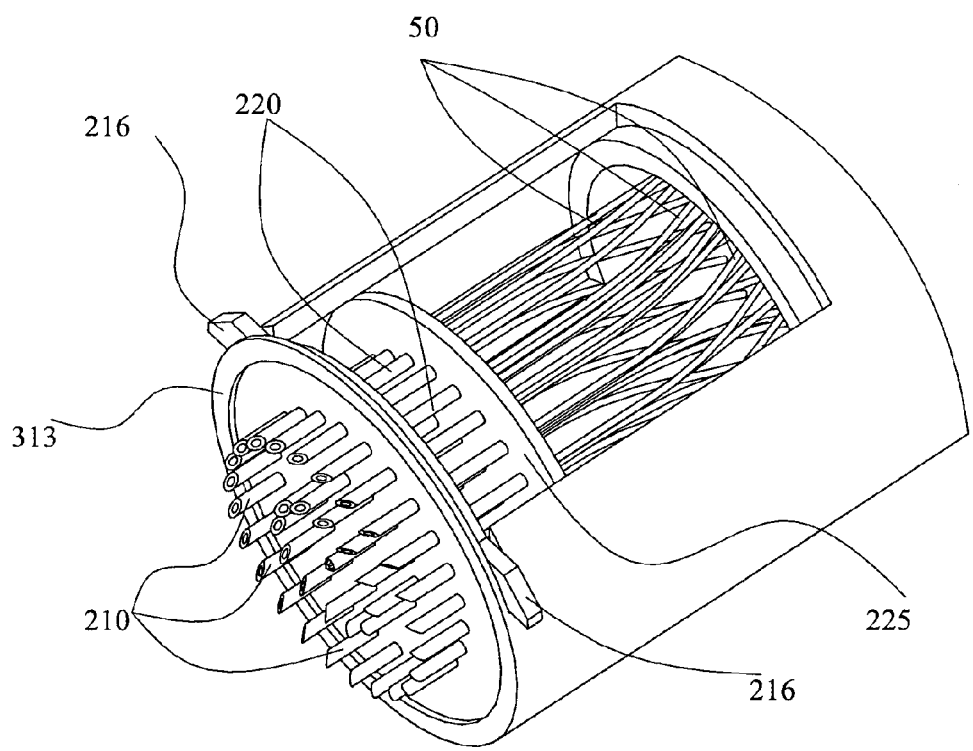
DETAIL B

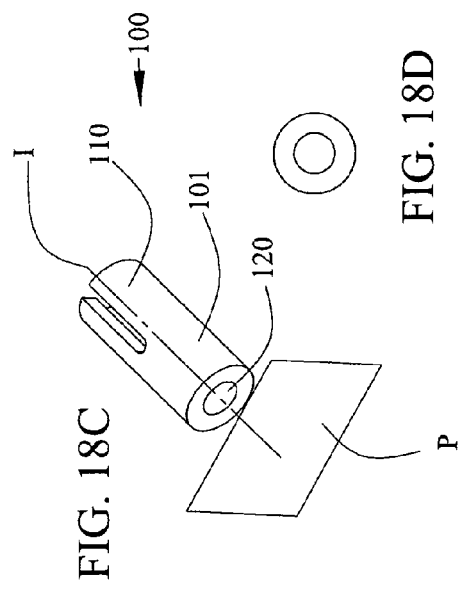
FIG. 18A
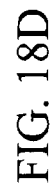
FIG. 18B
FIG. 18C
FIG. 18D
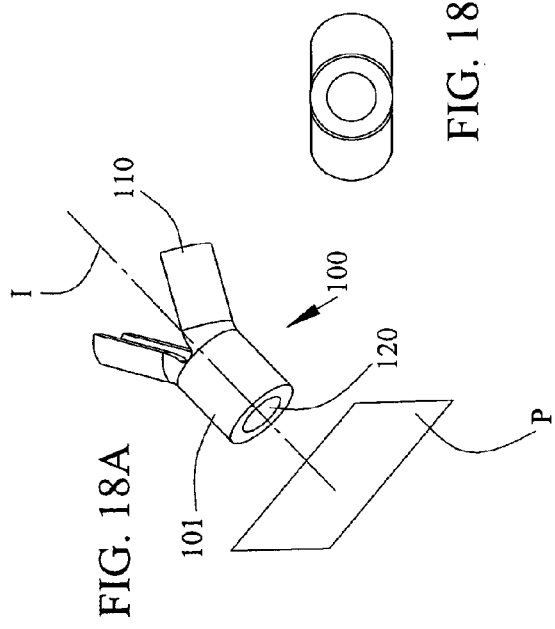
FIG. 18E
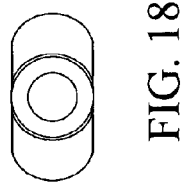
FIG. 18F
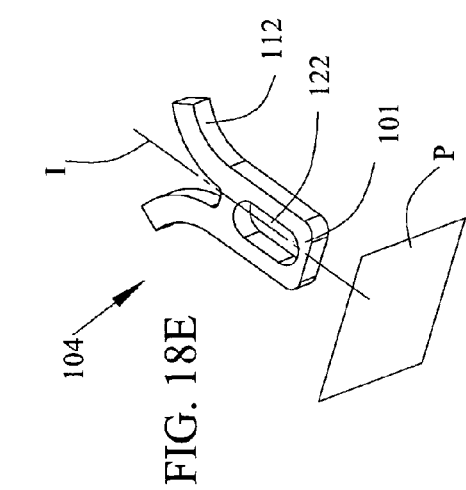
FIG. 18G
FIG. 18H

HAIR IMPLANT ANCHORS AND SYSTEMS AND METHODS FOR USE THEREOF

CROSS REFERENCE TO RELATED APPLICATIONS

The present application is a national phase application claiming benefit and priority from PCT/IL2010/000983 (published as WO 2011/064772), titled "Hair Implant Anchors and Systems and Methods for Use Thereof," filed Nov. 24, 2010 which in turn claims benefit and priority from U.S. Provisional Patent Application Ser. No. 61/283,045, filed Nov. 27, 2009, titled "Hair Implantation Device," both applications being hereby incorporated herein by reference in their entirety.

FIELD OF THE INVENTION

The present invention relates to hair implants, more specifically it relates to hair implant anchors, and systems and methods for use thereof.

BACKGROUND OF THE INVENTION

Baldness, alopecia, is a common phenomenon which often leads to general aesthetic dissatisfaction and sometimes even to psychological disorders. Seventy percent of males and 25 percent of females are, or will be, afflicted with some degree of baldness.

Non-surgical management of hair-loss, such as medical therapy and Minoxidil solution, has a temporary effect on baldness but the results are generally unsatisfactory. The use of wigs and toupees achieve only a cosmetic solution, generally providing poor aesthetic results. Surgical management remains the only permanent method of restoring hair; it includes hair transplants which make use of the patient's own hair and hair implants which use synthetic hair fibers.

One popular advanced surgical procedure, the Orentreich procedure, uses the patient's own hair and the transplant results in viable growing hair. A 1 cm wide skin strip (graft) is taken typically from the occipital part of the scalp of the patient and cut into small pieces. Each of these pieces contains typically 1-4 hair follicles. These small pieces are then surgically attached to the scalp typically using a microscope.

The Orentreich procedure is time consuming often requiring many sessions, is performed by a surgeon with the patient anesthetized and with a large support. The procedure results in scarring of the donation sites and requires a long recovery period. Importantly, it is fairly expensive and often produces less then satisfactory aesthetic results. The procedure is not suitable for all patients. It is not suitable in cases where there is no donation hair available or where there are burns on the scalp. It can, and often does, fail, since biological adoption of the transplanted hair is crucial for success. All these drawbacks deter people from using this technique.

Synthetic hair surgical procedures are "one hair at a time" procedures and they are anchored within the scalp by using knots or melt adhered loops in the hairs. This procedure is time consuming requiring many sessions, performed by a surgeon, and results in relatively large diameter insertions. Additionally, it is reported to have a yearly 20% failure rate due to poor anchoring. Typical synthetic hair implants use fibers and procedures developed by, for example, Medicap Ltd. of Italy and Nido Corp. of Japan.

SUMMARY OF THE INVENTION

The present invention seeks to provide an anchor to connect natural or synthetic hair to human tissue. Using the technique described herein, the hair and the target tissue are connected mechanically and artificially. Consequently, the hair may be successfully connected whether there is biological adoption or not.

The present invention provides a substantially self-deploying and self-anchoring anchor which is easily implanted into target tissue, suitable for treating progressive baldness. The device is suitable for hair implants in the scalp, eyebrow or other hair producing sites on the body. There is no scarring and the procedure can be completed in one or just a few sessions. The density and geometrical distribution of the hair being implanted may be varied as determined by the needs of the specific patient. The method of implanting the anchor described herein is also easy to use, and reduces the time required for treating a patient. Additionally, less of the implanted hair will fall out over time.

There is thus provided in accordance with one aspect of the invention, a hair implant anchor usable with a hair implant anchor deployment device for inserting one or more hairs into a tissue portion along an insertion axis substantially parallel to that portion of the longitudinal axis of each hair to be implanted within the tissue portion. The hair implant anchor comprises:

a holder configured to grip one or more hairs; and
one or more selectably deployable leaves formed with the holder, where in a first configuration of the anchor prior to implantation of the one or more hairs, the one or more leaves is constrained by the deployment device in a position generally parallel to the insertion axis, and in a second configuration of the anchor subsequent to insertion of the one or more hairs, the one or more leaves adopts a position extended away from the insertion axis, thereby securing the holder and the one or more hairs gripped thereby within the tissue portion.

In accordance with an embodiment of the anchor of the present invention, each hair has a bulbous root end for implantation into the tissue portion, and the holder has an opening sized so as to permit the diameter of the greater part of the hair to pass therethrough, and so as to prevent the passage therethrough of the bulbous root end of the hair.

According to another embodiment of the anchor of the present invention, at least the one or more selectably deployable leaves are formed from one of the following materials:

a. a shape memory material;
b. a superelastic material;
c. a resilient plastic material; and
d. a superabsorbent polymer.

In another embodiment of the anchor of the present invention, one or more of the following elements of the anchor is formed of nitinol: the at least one selectably deployable leaf and the holder.

In yet another embodiment of the anchor, the anchor is coated with an antibacterial or antimicrobial agent.

In yet another embodiment of the anchor, the holder includes a sized opening for preventing the passage therethrough of a bulbous end of the one or more hairs. The holder is substantially cylindrical and the one or more leaves are substantially parallel to the longitudinal axis of the cylindrical holder when the anchor is in its first configuration. When the one or more leaves are in the anchor's second configuration, the leaves extend away from the longitudinal axis of the cylindrical holder and extend beyond the lateral surface of the holder.

In yet another embodiment of the hair implant anchor, the holder of the hair implant anchor includes a sized opening therein for preventing the passage therethrough of a bulbous end of the at least one hair. The one or more leaves are generally parallel to the insertion axis when the one or more leaves are in the anchor's closed first configuration. The one or more leaves extend away from the insertion axis in the anchor's open second configuration. The projection of the anchor in the second configuration on a plane perpendicular to the insertion axis extends beyond the projection of the anchor on the plane when the anchor is in the closed first configuration.

In a further embodiment of the hair implant anchor, the holder is substantially a flat plate defining a plane having a sized opening formed in the plane of the plate for preventing the passage therethrough of a bulbous end of the one or more hairs. The one or more leaves are substantially coplanar with the plate when the anchor is in its first configuration, and is not coplanar therewith when in the second configuration.

In a still another embodiment of the anchor, the holder is substantially a flat plate defining a plane having a sized opening formed in the plane of the plate for preventing the passage therethrough of a bulbous end of the one or more hairs. The one or more leaves do not extend past the holder when the one or more leaves are constrained in the anchor's first configuration, and the one or more leaves extend past the holder when the anchor is in its second configuration.

In yet another embodiment of the anchor, the holder is substantially a flat plate defining a plane, the holder including a sized opening formed in the plane for preventing the passage therethrough of a bulbous end of the one or more hairs. The one or more leaves are substantially out of the plane when the anchor is in its first configuration prior to implantation of the one or more hairs and the one or more leaves are substantially coplanar with the plane when the leaves are in the anchor's second configuration. The holder is torqued when the anchor is constrained in the anchor's first configuration.

In another embodiment of the anchor, the anchor is formed of a resilient biodegradable material.

In another aspect of the present invention there is provided a method for hair implantation, comprising: inserting a hair into gripped engagement with a hair implant anchor having an open and a closed configuration, thereby providing a preloaded hair implant anchor; inserting the preloaded hair implant anchor through the skin of a patient while constraining the anchor to remain in its closed configuration; and releasing the anchor so as to cause a subcutaneous deployment thereof and such that the anchor transitions to its open configuration, thereby securing the anchor and the hair gripped therein to subcutaneous tissue.

In another embodiment of the method, the method further includes the step of providing a hair implant anchor delivery device having a delivery needle, and placing the preloaded hair implant anchor into the needle.

In another embodiment of the method, the step of releasing further comprises the step of pushing a pusher of the hair implant anchor delivery device so as to cause subcutaneous deployment of the anchor.

In the embodiments of the method, the hair implantation anchor is constructed substantially as recited above.

In yet another aspect of the present invention there is provided a hair implantation system for inserting one or more hairs into a tissue portion along an insertion axis substantially parallel to that portion of the longitudinal axis of each hair to be implanted within the tissue portion. The system comprises a hair implant anchor constructed substantially as recited above and a hair implant anchor delivery device. The delivery device comprises a needle and a pusher. The needle comprises a tubular stem and a handle attached to the stem, the needle having a free end operative to pierce target tissue in which the hair is to be implanted and to deliver into the target tissue the hair implant anchor positioned in the tubular stem while the anchor is in its constrained closed configuration. The pusher comprises an elongated stem and a handle attached thereto. The elongated stem of the pusher is positioned within the tubular stem of the needle, the pusher operative to push the hair implant anchor out of the needle and into the target tissue allowing the anchor to transition to its open configuration, anchoring the anchor and hair within to the tissue.

In an embodiment of the hair implantation system, each hair has a bulbous root end for implantation into the target tissue, and the holder has an opening sized so as to permit the diameter of the greater part of the hair to pass therethrough and so as to prevent the passage therethrough of the bulbous root end of the hair.

In yet another embodiment of the hair implantation system, the one or more selectably deployable leaves are formed from one of the following materials:
  a. a shape memory material;
  b. a superelastic material;
  c. a resilient plastic material; and
  d. a superabsorbent polymer.

In a further embodiment of the hair implantation system, the hair implant anchor is coated with an antibacterial or antimicrobial agent.

In still another embodiment of the hair implantation system, the elongated stem of the pusher is selected from the following: a rod, a tubular stem and a tubular stem partially cut away in the longitudinal direction of the tube.

In yet another embodiment of the hair implantation system, the holder of the hair implant anchor includes a sized opening therein for preventing the passage therethrough of a bulbous end of the one or more hairs. The holder is substantially cylindrical. The one or more leaves are substantially parallel to the longitudinal axis of the cylindrical holder when the one or more leaves are in the anchor's first configuration, and the one or more leaves extend away from the longitudinal axis of the cylindrical holder and extend beyond the lateral surface of the holder when the leaf is in the second configuration.

In still another embodiment of the hair implantation system, the holder of the hair implant anchor includes a sized opening therein for preventing the passage therethrough of a bulbous end of the at least one hair. The one or more leaves are generally parallel to the insertion axis when the one or more leaves are in the anchor's closed first configuration. The one or more leaves extend away from the insertion axis in the anchor's open second configuration. The projection of the anchor in the second configuration on a plane perpendicular to the insertion axis extends beyond the projection of the anchor on the plane when the anchor is in the closed first configuration.

In yet another aspect of the present invention there is provided a multi-hair implantation system including: a cartridge comprising a plate and a plurality of hair implantation systems connected thereto, each hair implantation system constructed substantially as recited above; and a handle. The handle is constructed and operative to eject the plurality of hair implant anchors into target tissue allowing the anchors to transition from their closed first configuration to their open second configuration anchoring the hair implant anchors and the one or more hairs therein within the target tissue.

In yet another embodiment of the multi-hair implantation system the handle can be manipulated to allow the needles of the hair implantation systems to penetrate target tissue at a preselected angle with respect to the longitudinal axis of the handle.

In another aspect of the present invention there is provided a hair implantation assembly for implanting hair, usable with a hair implant anchor deployment device. The assembly comprises at least one hair having a hair shaft and a bulbous hair bulb on an end of the hair shaft and a hair implant anchor. The anchor comprises a holder and one or more deployable leaves. The holder includes a sized opening operative to prevent the bulbous hair bulb from being pulled through the opening. The anchor has a closed position when the anchor is positioned within, and the one or more leaves are constrained by, the hair implant anchor deployment device. The anchor has an open position when the anchor is positioned outside the deployment device and subcutaneously. In the open position the one or more deployable leaves extend past the holder, thereby securing the hair implantation assembly to tissue.

In an embodiment of the hair implantation assembly, the one or more selectably deployable leaves are formed from one of the following materials:
  a. a shape memory material;
  b. a superelastic material;
  c. a resilient plastic material; and
  d. a superabsorbent polymer.

In another embodiment of the hair implantation assembly, the bulbous end of the hair is formed by one of the following methods.

In a further embodiment of the hair implantation assembly, the hair implant anchor is coated with an antibacterial or antimicrobial agent.

In yet another embodiment of the hair implantation assembly, the hair is selected from the group consisting of the following: a hair formed of synthetic fiber, a non-viable human hair that can not grow in its new environment after implantation, and a viable human hair that can grow in its new environment after implantation.

In a further embodiment of the hair implantation assembly, the hair implant anchor is formed of a resilient biodegradable material.

In another aspect of the present invention there is provided a hair implantation system for inserting one or more hairs into a tissue portion along an insertion axis substantially parallel to that portion of the longitudinal axis of each hair to be implanted within the tissue portion. This system comprises a hair implantation assembly constructed substantially as recited above and a hair implant anchor delivery device comprising a needle and a pusher. The needle comprises a tubular stem and a handle attached to the stem and has a free end operative to pierce target tissue in which the hair is to be implanted and to deliver into the target tissue the hair implant anchor positioned in the tubular stem while in its constrained closed configuration. The pusher comprises an elongated stem and a handle attached thereto, the elongated stem of the pusher positioned within the tubular stem of the needle. The pusher is operative to push the hair implant anchor out of the needle and into the target tissue allowing the anchor to transition to its open configuration anchoring the anchor and hair within to the tissue.

In another aspect of the present invention there is provided a multi-hair implantation system comprising a cartridge and a handle. The cartridge comprises a plate and a plurality of hair implantation systems connected thereto, each hair implantation system constructed substantially as recited above. The handle is constructed and operative to eject the plurality of hair implant anchors into target tissue allowing the anchors to transition from their closed first configuration to their open second configuration anchoring the hair implant anchors and the one or more hairs therein within the target tissue.

BRIEF DESCRIPTION OF THE DRAWINGS

The present invention will be more fully understood and its features and advantages will become apparent to those skilled in the art by reference to the ensuing description, taken in conjunction with the accompanying drawings, in which:

FIG. 10 is a perspective view of a handle for use in effecting implantation of hairs held in the cartridge shown in FIGS. 8-9;

FIG. 11 is a perspective view of a multi-hair implantation system comprising the handle shown in FIG. 10 loaded with a cartridge constructed as in FIGS. 8-9, the cartridge including a plurality of hair implant anchor delivery devices each operative to implant a hair;

FIGS. 18A-18H show the projections of two anchors constructed according to the present invention in their closed and open configurations.

DETAILED DESCRIPTION OF PREFERRED EMBODIMENTS OF THE INVENTION

Figure 2:
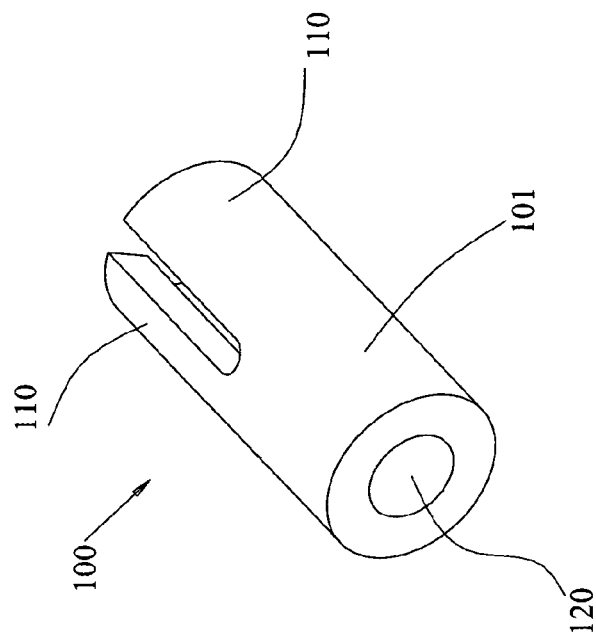
FIG. 2 is a perspective view of a first embodiment of a self-deploying hair implant anchor in its closed configuration constructed according to the present invention.

In general, the method of the present invention utilizes a miniature self-deploying element, herein designated as a hair implant anchor, which mechanically attaches hair to target tissue.

Before explaining several embodiments of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

"Distal" in the context of the anchors, assemblies, devices, and systems discussed herein, indicates that portion of the anchor, assembly, device or system closest to the target tissue into which one or more hairs are to be implanted.

The use of the terms "tissue", "tissue portion", "target tissue" and the like are used interchangeably herein.

Figure 1:
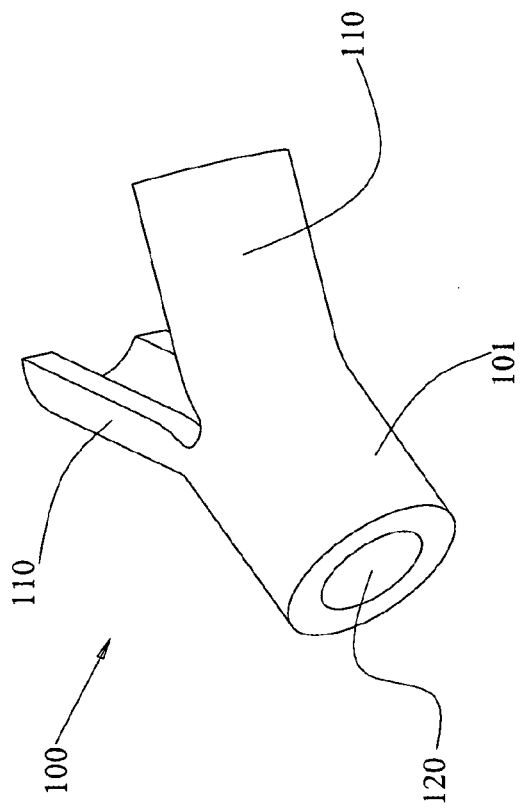
FIG. 1 is a perspective view of a first embodiment of a self-deploying hair implant anchor in its open configuration constructed according to the present invention.

Reference is made to FIGS. 1 and 2 which illustrate a self-deploying hair implant anchor 100, and its open and closed configurations respectively, the anchor constructed according to an embodiment of the present invention. Anchor 100 comprises a holder 101 with an opening 120 therethrough and at least one leaf 110 typically integrally joined to the holder of the anchor. The anchor's closed and open configurations may also be designated in the specification and claims as its first and second configuration, respectively.

Anchor 100 has typical, but non-limiting, dimensions of an outer diameter of 0.15-0.3 mm, an internal diameter of 0.08-0.2 mm and an overall height of 0.15-0.5 mm. These tiny dimensions enable hair implant anchor 100 to be implanted subcutaneously while keeping a normative anatomy. The implants may be placed in the head under the scalp, under the eyebrow, or in any place on the body where hair needs to be replaced and/or hair loss corrected.

Anchor 100 may be constructed from resilient materials. It may be constructed from a superelastic metal such as, but not necessarily limited to, nitinol, or, alternatively, it may be constructed from an elastic polymer material such as, but not necessarily limited to, polyetheretherketone (PEEK), ultra high molecular weight polyethylene (UHMWPE), silicone, polyetherimide, or the like.

In other embodiments, a shape memory alloy (SMA), such as, but necessarily limited to, nitinol, may be used to construct the anchor. When utilizing the SMA property, prior to implantation of the anchor, the anchor is maintained at a temperature lower than human body temperature. Typically it is kept at room temperature. When the anchor is injected into the body as with a delivery system described hereinbelow, the anchor warms to body temperature. When using a nitinol anchor, body temperature can typically be above the alloy's austenitic final temperature ($A_f$). Once the anchor is heated to above its $A_f$ temperature, the anchor automatically deploys and the anchor transitions from its closed configuration to its open configuration as described herein.

Other polymeric materials that may also be used to construct anchor 100 are superabsorbent polymers. These are cross-linked polymers which expand when absorbing water. A typical superabsorbent polymer is sodium polyacrylate.

In some embodiments of the present invention, the anchor may be formed as a composite with, for example, the holder formed of one material and the leaves formed from a second material, the second material being a resilient material. The resilient material may be a superelastic material, a shape memory alloy, or a resilient plastic material as discussed above.

In FIG. 1, anchor 100 is shown in its open configuration that is the anchor's configuration when no constraining force is being applied. In its unconstrained shape, anchor 100 has at least one leaf 110 in its open position that is extending away from holder 101 of anchor 100. In FIG. 1, an anchor having two leaves is shown; in other embodiments, the anchor may have more than two leaves or a single leaf.

Holder 101 of hair implant anchor 100 has a sized insertion opening 120 through which most of the shaft of a hair is inserted. Due to the opening's size, only the hair's shaft passes through opening 120. The hair's bulbous end, that is the hair bulb, has at least one dimension larger than the dimension of opening 120 and therefore can not pass through the opening.

The "opening" may also be designated herein as a "hole", "slit", or "aperture"; these terms may be used herein as synonyms for "opening" without any intent at distinguishing between them.

In what is described herein, the leaves and holder of the anchor are integrally formed. It is however contemplated that in some embodiments the leaves and holder may be non-integral with each other.

In FIG. 2, anchor 100 is shown in its constrained closed configuration where leaves 110 are in their closed position that is in a position where they do not extend away from holder 101. The constrained closed configuration is the anchor's configuration when it is positioned in a hair implant anchor deployment device to be discussed below. The hair anchor deployment device may herein be denoted as a hair anchor delivery device without any intent at distinguishing between the terms.

Anchor 100 may be used with synthetic or natural hair. Synthetic hair is constructed to have a thin shaft and an artificial hair bulb at the distal end of the shaft. Natural hair includes a thin shaft and either a natural hair bulb or an artificial hair bulb at the distal end of the shaft. Artificial hair bulbs or enhanced natural hair bulbs may be made using one or more adhesives or by using heat treatment or any other method known to those skilled in the art for producing artificial bulbous hair bulbs. After implantation of a hair, part of the hair shaft lies within the target tissue while generally, a larger portion of the shaft extends outside the body.

In the case of natural hair with a natural hair bulb, additional portions of the original follicular structure may remain attached to the hair bulb. The natural bulb and its residue of living material from the hair's original follicle may then, in optimal situations, result in a viable implant capable of growing in its new post-implantation environment.

When synthetic hair is used it may be made of monofilament or multi-filament synthetic materials. The synthetic hair may be formed from, but without intending to limit the invention, polyamides, polyethylene terephthalate (PET), polybutylene terephtalate (PBT) or the like.

The fibers may be coated with other materials such as collagen, silver which can function as an antimicrobial, or other antibiotic materials.

The hair may be pre-colored, for example, with commercially available hair dyes. In the case of synthetic hair formed of polymers, coloring pigments, including inorganic pigments, may be added to the polymer during processing.

Figure 4:
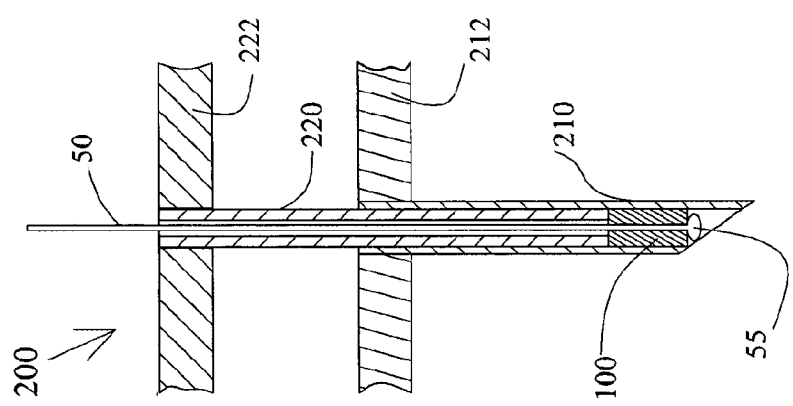
FIG. 4 shows a schematic cross-sectional view of a hair being held by the hair implant anchor delivery device of FIG. 3 prior to the hair's implantation.
Figure 3:
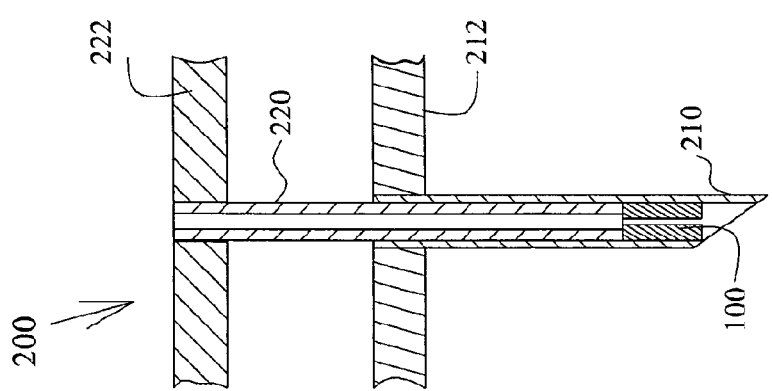
FIG. 3 shows a schematic cross sectional view of a hair implant anchor positioned inside a delivery device used in delivering the self-deploying anchor of FIGS. 1 and 2.

Reference is now made to FIGS. 3 and 4 which show a hair implant anchor deployment device 200 that can be used to deploy a hair implant anchor such as anchor 100 shown in, and discussed in conjunction with, FIGS. 1 and 2. Device 200 includes a needle 210 and a pusher 220. Both needle and pusher have tube-like constructions with handles, 212 and 222, respectively, projecting substantially transversely therefrom. The tube-like portion of pusher 220 fits substantially concentrically within the tube-like portion of needle 210.

FIG. 3 shows hair implant anchor deployment device 200 and anchor 100 positioned within but without a hair to be implanted. FIG. 4 shows anchor 100 with the hair to be implanted positioned therein. In FIG. 4, hair implant anchor deployment device 200 is deemed to be loaded; it is designated as being loaded when anchor 100 is in its closed configuration inside device 200 and a hair is positioned within opening 120 of anchor 100 ready for implantation.

To load device 200, the user inserts the shaft of hair 50 through opening 120 of hair implant anchor 100 positioned in device 200 therein and then through the tubular section of device 200. Hair bulb 55, either a natural or artificial bulb, being generally bulbous and thicker than the hair shaft is physically trapped beneath anchor 100. "Beneath anchor 100" refers to the distal side of anchor 100. When loaded in device 200, the longitudinal axis of the hair shaft, at least that portion that will remain implanted within the target tissue, is positioned substantially parallel to the axis of insertion of needle 210. In the closed first configuration, the one or more leaves of anchor 100 are constrained by deployment device 200 in a position generally parallel to the insertion axis.

"Insertion axis" as used herein is the axis along which the deployment device inserts the hair being implanted into the tissue. It is determined by the point of the target tissue wherein the anchor and hair enter the tissue ("point of penetration"). When the deployment device is essentially linear, the insertion axis extends from the point of penetration and is substantially parallel with the longitudinal axis of the deployment device. In many instances, the insertion axis may be collinear with the longitudinal axis of the deployment device.

Figure 5:
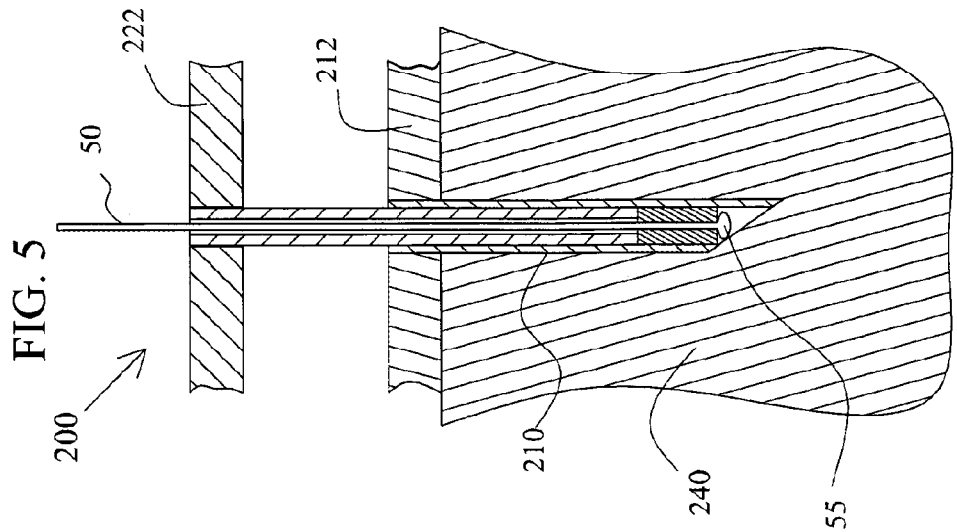
FIGS. 5-7 illustrate the method of operation of the hair implant anchor delivery device of FIGS. 3-4 and resultant implantation of the hair in FIG. 4.
Figure 7:
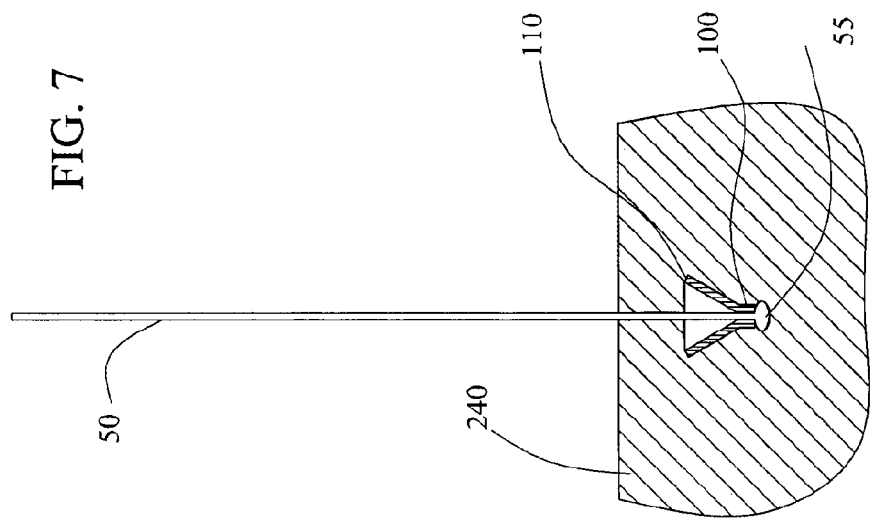
Figure 6:
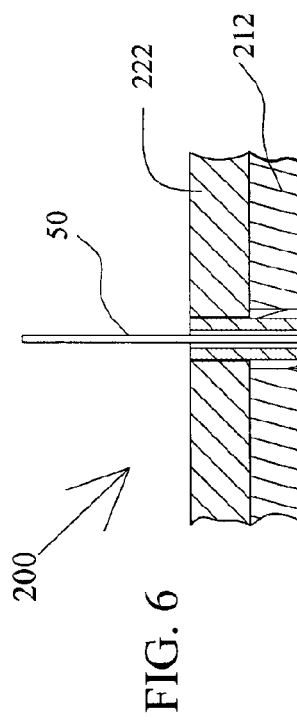
Figure 6:
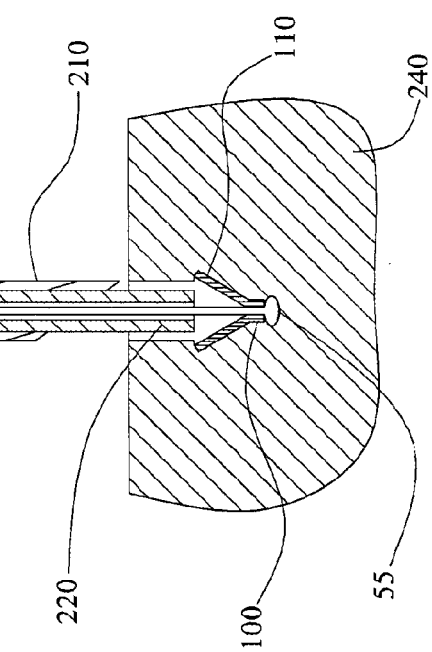

In FIGS. 5 through 7, to which reference is now made, the steps of the generic method for implanting anchor 100 are illustrated in sequential order. For simplicity, the use of a single hair with anchor 100 is shown in FIGS. 4-7, but it can readily be understood by persons skilled in the art that a plurality of hairs may be placed into and constrained within a single anchor 100 and then implanted.

In FIG. 5, a user utilizes device 200 to penetrate target tissue 240 with needle 210. Needle 210 may penetrate target tissue 240 until needle handle 212 is substantially adjacent to the tissue. In order to ease penetration, needle 210 is provided with a distal sharp end.

In FIG. 6, the user using needle handle 212 pulls needle 210 in the proximal direction out of target tissue 240. The needle moves relative to pusher 220. As a consequence, constrained anchor 100 is pushed out of needle 210 by the distal end of the tubular portion of pusher 220 leaving anchor 100 within target tissue 240. At that stage, the anchor's leaves 110 automatically deploy, that is they extend outwards from holder 101 of anchor 100, and the anchor transitions to its open configuration. As illustrated by way of example in FIGS. 6 and 7, the anchor is sized to be implanted fully contained within the scalp or eyebrow target tissue with a longitudinal axis of the anchor transverse to the external surface of the scalp or eyebrow target tissue. As described later in greater detail, the anchor may be implanted normal to the external surface or at an angle with respect to the external surface.

In the open second configuration of anchor 100 of FIG. 1 and anchors 102, 104, 106, and 108 of FIGS. 12, 13, 14, and 15, respectively, the one or more leaves of the anchors extend away from the insertion axis. The projection of the anchor in its open second configuration on a plane perpendicular to the insertion axis, extends beyond the projection of the anchor on the plane when the anchor is in its closed first configuration.

Figure 13:
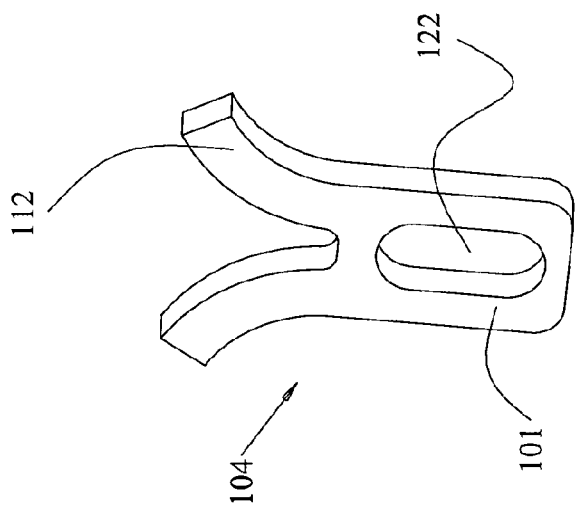

Reference is now made to FIGS. 18A-18H which illustrate the projections of two anchors, anchor 100 in FIGS. 1 and 2 discussed above and anchor 104 discussed below in conjunction with FIG. 13. In the drawing "I" represents the insertion axis and "P" the plane perpendicular to "I" on which the projection is cast. The numbered elements of anchor 100 have been discussed in conjunction with FIGS. 1 and 2 above. The elements of anchor 104 shown in FIG. 18E and discussed below in conjunction with FIG. 13 are a holder 101, an opening 122 and deployable leaves 112. FIGS. 18B, 18D, 18F and 18G represent the projection of the anchors in FIGS. 18A, 18C, 18E and 18G, respectively, on the plane P. As readily seen, the projection of anchor 100 in its open configuration, as seen in FIG. 18B, extends beyond the projection of anchor 100 in its closed configuration, as seen in FIG. 18D. Similarly, the projection of anchor 104 in its open configuration, as seen in FIG. 18F, extends beyond the projection of anchor 100 in its closed configuration as seen in FIG. 18H.

Finally, in FIG. 7, device 200 is removed by pulling handles 212 and 222 away from tissue 240 leaving hair 50 implanted in target tissue 240. Hair 50 remains mechanically trapped inside hair implant anchor 100. Since anchor 100 is formed of resilient material or a superabsorbent polymer it applies a compressive force on the tissue. Due to the anchor's shape after deployment, that is, due to its open configuration, hair 50 is geometrically secured against movement out of the target tissue.

It is readily understood that the implantation of anchor 100 can also be viewed and described from the perspective of pusher 220 as follows. After insertion of needle 210 (FIG. 5) pusher handle 222 is advanced distally in the direction of target tissue 240. Pusher 220 thereby "pushes" anchor 100 out of needle 210 at which stage the anchor's leaves 110 automatically deploy transitioning to their open configuration.

Reference is now made to FIGS. 8 through 11 which illustrate a multi-hair implantation system 400. System 400 includes a cartridge 250 and a reusable or disposable handle 300. Cartridge 250 in turn includes a plurality of hair implant anchor deployment devices 200, each of which is comprised of a needle 210 and a pusher 220 as shown in FIGS. 3 and 4 and described in conjunction therewith. When deployment device 200 is preloaded it includes a hair implant anchor 100 holding at least one hair 50 substantially as shown in FIG. 4 and described in conjunction therewith.

Figure 8:
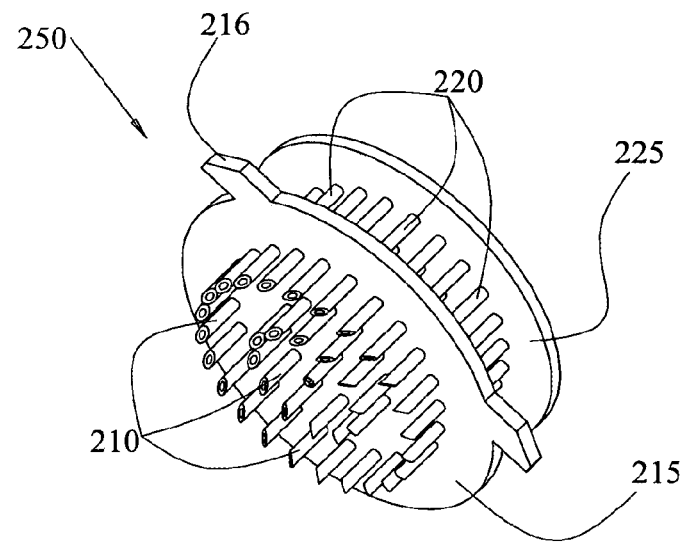
FIGS. 8-9 are perspective views of one embodiment of a cartridge device for simultaneous implantation of a plurality of hairs, each hair implanted by a hair implant anchor delivery device substantially similar to that shown in FIGS. 3-7.

The initial configuration of cartridge 250 is shown in FIG. 8. Cartridge 250 includes a plurality of needles 210, and multiple pushers 220, to effect multiple simultaneous hair implantations. The number of needles and their geometrical distribution, e.g. linear, circular, elliptical, etc., vary according to the user's needs. These different distributions allow the anchor to be used for scalp and eyebrow implants as well as for treating different types of receding hairlines. The user can select the optimal number and/or geometrical distribution of needles 210 in cartridge 250. Preferably, inside each needle 210, anchor 100 (not shown) is already pre-loaded.

Preferably, all of the needles 210 are rigidly connected to distal plate 215, and preferably all the pushers 220 are rigidly connected to proximal plate 225. Typically, but without intending to limit the invention, these rigid connections may be formed by using a laser welding machine and/or adhesives such as epoxy adhesives, and/or by using ultrasonic welding and/or any other suitable method known to those skilled in the art.

Figure 9:
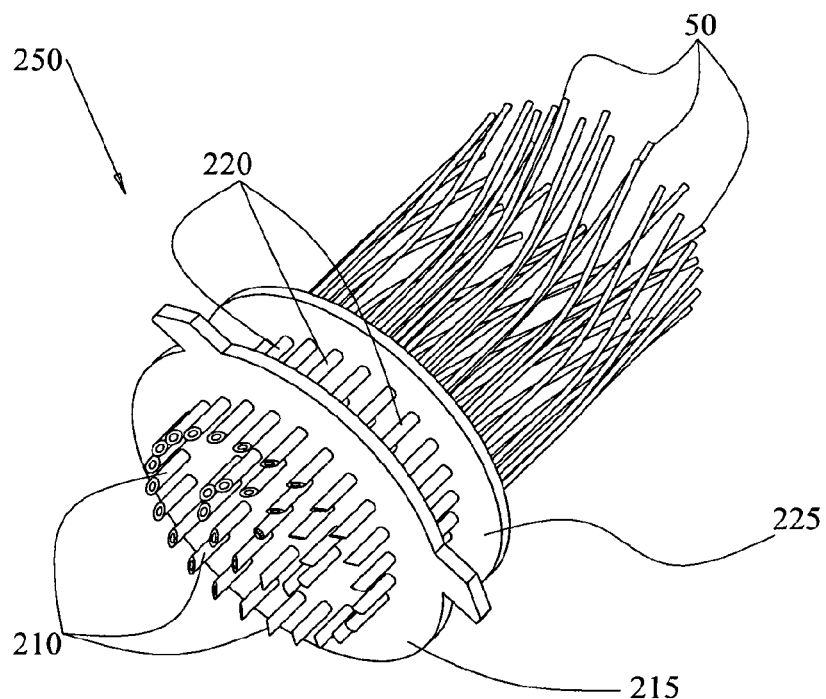

Needles 210 and pushers 220 are preferably made from stainless steel tubing and distal plate 215 and proximal plate 225 are preferably made from stainless steel plates, but other materials known to those skilled in the art may also be used. Typically, but without intending to limit the invention, the tubing and plates may be produced by using a laser cutting machine and/or by using chemical etching, and/or by using micro molding, and/or any other suitable method known to those skilled in the art. In FIGS. 8 and 9, as in FIGS. 3 and 4, the tube portion of pusher 220 is positioned within and concentrically with the tube portion of needle 210.

Distal plate 215 optionally includes positioning ears 216, to enable proper positioning of cartridge 250 inside handle 300 (discussed below), and to allow for quick removal of cartridge 250 from handle 300 thereby enabling quick re-loading.

Cartridge 250 may be constructed so that plate 215 may be fixedly maintained transverse to the longitudinal axis of handle 300 (FIGS. 10 and 11). When handle 300 positions cartridge 250 so that plate 215 is positioned substantially parallel to the scalp, the angle of all the needles 210 of cartridge 250 are essentially normal to the scalp. Accordingly, they penetrate the scalp to essentially the same depth. If, for better aesthetic results, handle 300 is manipulated so that plate 215 is effectively positioned at an angle with respect to the scalp, all of needles 210 enter the scalp at the same angle. Presumably, in some instances when a very large cartridge is used or when the cartridge is positioned against the scalp at a very large angle, some of the needles only partially penetrate the scalp or do not penetrate the scalp at all. It should be understand that cartridges with needles of various lengths can be used to provide holes of uniform depth when penetrating at an angle. It should also be readily understood by one skilled in the art that uniform depth can be achieved using cartridges having needles of different needle length and penetration angles.

The control of the angle has an impact on aesthetics since the angle of human hair varies in going from one area of the scalp to another. There are also differences in hair angle when comparing one race to another. In places where the physician would prefer to penetrate the scalp at a sharp angle he could work with a cartridge having only a single row of deployment devices.

In general, plate 215 is a safety measure not present in current implantation devices. Plate 215 limits maximal penetration of the needles preventing damage resulting from over penetration.

As shown in FIG. 9, the user inserts hairs 50 through anchors 100 which are not shown as they are obscured by needles 210 and then through needles 210 of cartridge 250. Hairs 50 are also passed through pushers 220 of cartridge 250. Cartridge 250 is then ready for loading into handle 300.

It should be noted that preferably the cartridges are pre-loaded. A hair implant anchor 100 is loaded to grip at least one hair. The loading occurs with the hair shaft being "threaded" so as to pass through the opening of the anchor while the larger dimensioned bulbous hair bulb, natural or artificial, is blocked by the opening. A loaded anchor is then inserted into a needle 210 of cartridge 250 and the at least one hair of the anchor is inserted into and pulled through the needle 210 and its associated pusher 220. This is repeated for each needle/pusher combination of the cartridge. It is contemplated that the user performing the hair implant will not have to prepare the cartridges. The cartridges will be provided fully preloaded by a supplier for immediate insertion into handle 300.

FIG. 10 demonstrates a reusable or disposable handle 300. Handle 300 comprises an external tube 310, an internal injector 330, and a return spring 350. Handle 300 may typically be formed of reusable, steamable, i.e. disinfectable, materials such as stainless steel, polyphenylsulfone or the like. Alternatively, handle 300 may be made from inexpensive disposable materials such as polycarbonate, polyethylene terephthalate (PET) and the like. Additionally, they may also be made from a combination of these materials.

Arms 315, which may be rigidly connected to external tube 310, and button 334, which may be rigidly connected to internal injector 330, are ergonomic elements enabling the user to hold and operate handle 300 comfortably. Pin 336 may be rigidly connected to internal injector 330 and is geometrically constrained by slit 316 positioned in external tube 310. When button 334 is not pressed, return spring 350 insures that internal injector 330 is positioned at its proximal position relative to handle 300. When button 334 is pressed, pin 336 and slit 316 limit the relative motion of external tube 310 with respect to internal injector 330.

As shown in FIG. 10, detail A, external tube 310 includes a distal slit 314, and internal injector 330 includes upper slit 334, both of which allow loading cartridge 250 into handle 300. Slits 314 and 334 are in registration with each other allowing quick loading of cartridge 250. Optionally, external tube 310 may also have an internal slit 317 and side slits 312, which secure cartridge 250 once it is inserted into handle 300.

Optionally, the distal end of handle 300 may be formed of a flexible/resilient material which allows for a snap-on interface between handle 300 and cartridge 250. Cartridges 250 may be snapped on when loaded onto handle 300 and removed after the implant procedure has been completed and/or the cartridge expended.

FIG. 11 illustrates multi-hair implantation system 400 in its assembled configuration with loaded cartridge 250 inserted into handle 300, and ready for use.

To perform hair implantations with pre-loaded multi-hair implantation system 400, the user follows the procedures outlined below.

Distal surface 313 of external tube 310 is held and pressed against the target tissue and button 334 is pressed causing it to move toward handle arms 315. Consequently, surface 335 of internal injector 330 shown in FIG. 10, presses on proximal plate 225 (FIGS. 8 and 9) which in turn pushes against pushers 220. This in turn pushes on the plurality of loaded hair implant anchors (not shown) within needles 210 (FIGS. 8 and 9) discharging them into the target tissue allowing the anchors to transition to their open configuration as described in conjunction with FIGS. 1 through 7 above.

Finally, the user removes system 400 after hairs 50 have been implanted, as described above. If additional implantations are required, the user simply removes expended cartridge 250, preferably by using ears 216 or by pushing it through a slit (not shown) in the handle's distal end, and inserts another pre-loaded cartridge 250 as shown in FIG. 9 into handle 300.

Figure 14:
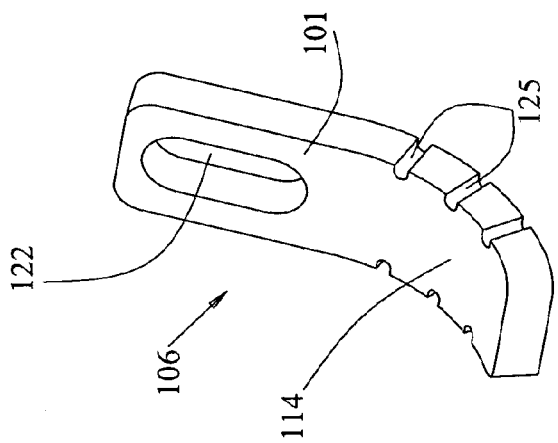
FIGS. 12-15 are perspective views of additional embodiments of self-deploying anchors constructed according to the present invention.
Figure 12:
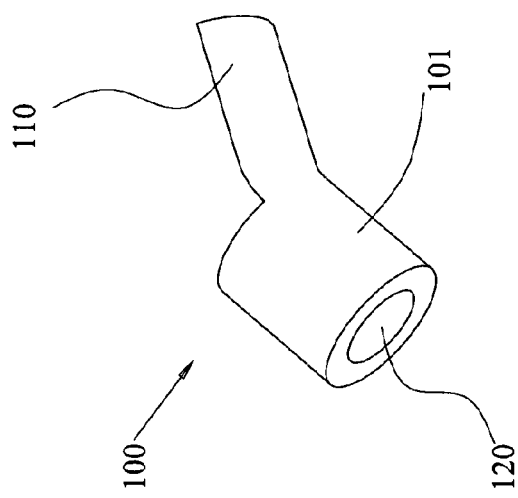

FIG. 12 to FIG. 14, to which reference is now made, illustrate additional hair implant anchor embodiments. Anchor 102 in FIG. 12 is similar to anchor 100 of FIGS. 1 and 2 but has only one leaf. Anchor 104 and anchor 106 shown in FIG. 13 and FIG. 14, respectively, are typically but without intending to limit the invention, formed from a nitinol plate. Typically, the plate may be cut by using a laser cutting machine. Hair 50, not shown in FIG. 13 and FIG. 14, is inserted through slit 122. As in anchor 100 of FIGS. 1 and 2 and anchor 102 of FIG. 12, slit 122 is sized to be smaller than the natural or artificial hair bulb of a hair preventing the hair's disengagement from anchor 104 and 106. Slit 122 of FIGS. 13 and 14 is positioned to allow hair 50 to be placed relatively parallel to anchors 104 and 106. Anchor 104 has two open leaves 112, while anchor 106 has one open leaf 114 integrally formed with holder 101. Anchor 106 is formed with a rough surface 125 so that the force required to dislodge a hair from target tissue is enhanced.

Figure 15:
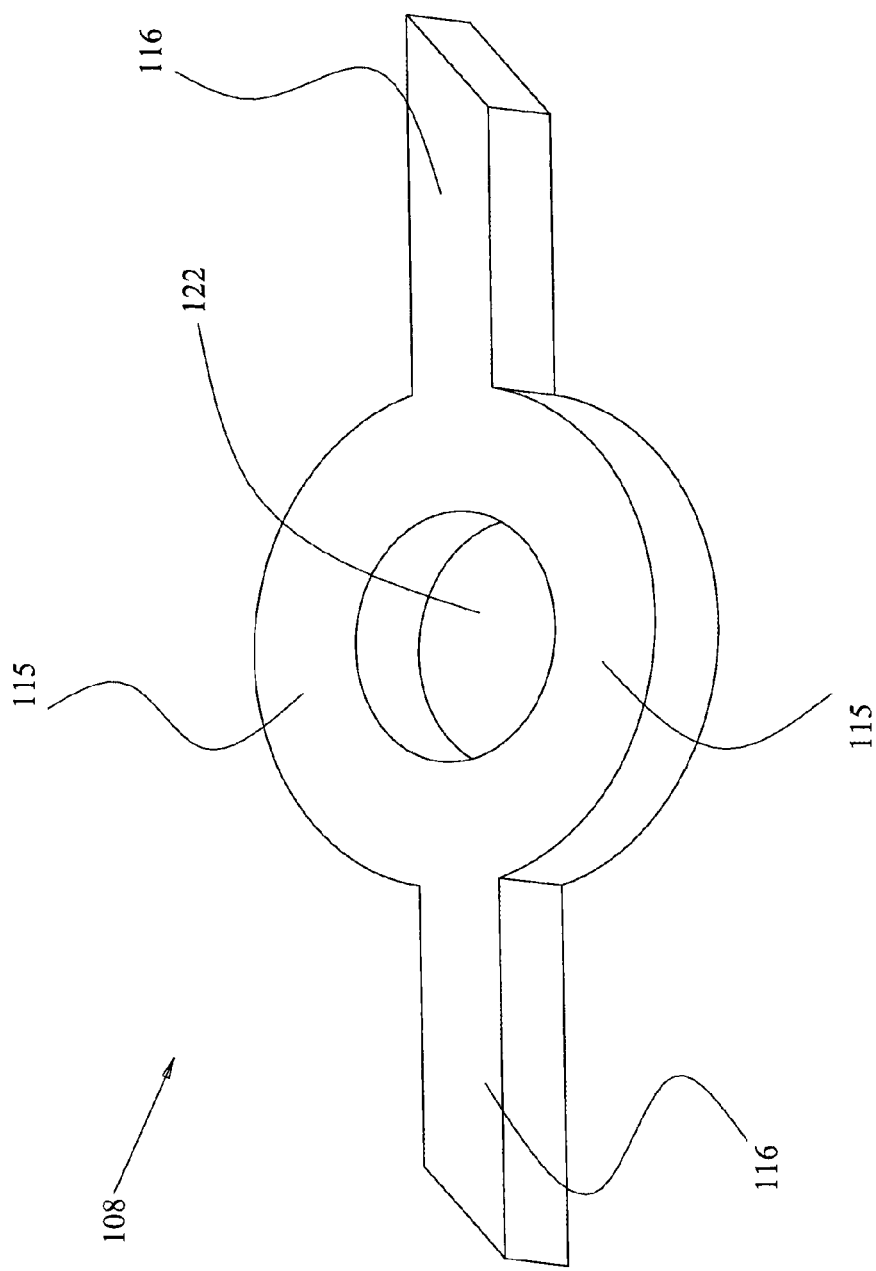

FIG. 15 shows another embodiment of an anchor constructed and operative according to the present invention. Anchor 108 is cut from a nitinol sheet so as to include a holder 115, an opening 122 and a pair of leaves 116. A hair stem passes through opening 122, the opening being sized to restrain the bulbous end, the hair bulb, of the hair from passing through. When inserted into a needle of a hair implant anchor deployment device, the anchor is constrained to transition from its extended open configuration shown in FIG. 15 to its closed configuration. In the latter, the leaves fold towards holder 115 and holder 115 may twist relative to leaves 116 somewhat. After anchor 108 is deployed, it transitions back to its open configuration that is the configuration shown in FIG. 15, thereby securing the anchor and hair within the anchor to the target tissue. Since anchor 108 is produced from a sheet, it is less expensive and easier to produce than an anchor having a tubular i.e. cylindrical construction. Anchor 108 can be deployed using a deployment device substantially similar to the one shown in, and described in conjunction with, FIGS. 3 and 4.

Optionally, if anchor 108 or any of the other hair implant anchors described herein is formed from a shape memory alloy (SMA), the anchor may be loaded into the needle by first cooling it to a temperature below its austenitic temperature and in its martensitic state. Using an anchor formed from a shape memory alloy having an austenitic transition temperature dramatically decreases the forces required for loading the anchor. The needle is not what constrains the anchor in its closed first configuration. The constraint is produced by the martensitic state of the alloy. Upon ejection from the needle and return of the anchor's temperature to a temperature above the material's austenitic transition temperature, the alloy transitions to its superelastic state and the anchor transitions to its open second configuration.

When using an SMA anchor, a delivery system slightly altered from the ones described in conjunction with FIGS. 3 and 4 above and FIG. 16 to be discussed below may be used. The target tissue may be pierced using a conventional needle and the implant anchor can then be pushed by using any suitable instrument directly into the tissue. After the anchor has been placed into the tissue, the anchor's temperature rises above its austenitic temperature, and the anchor transitions to it open second configuration.

Figure 16:
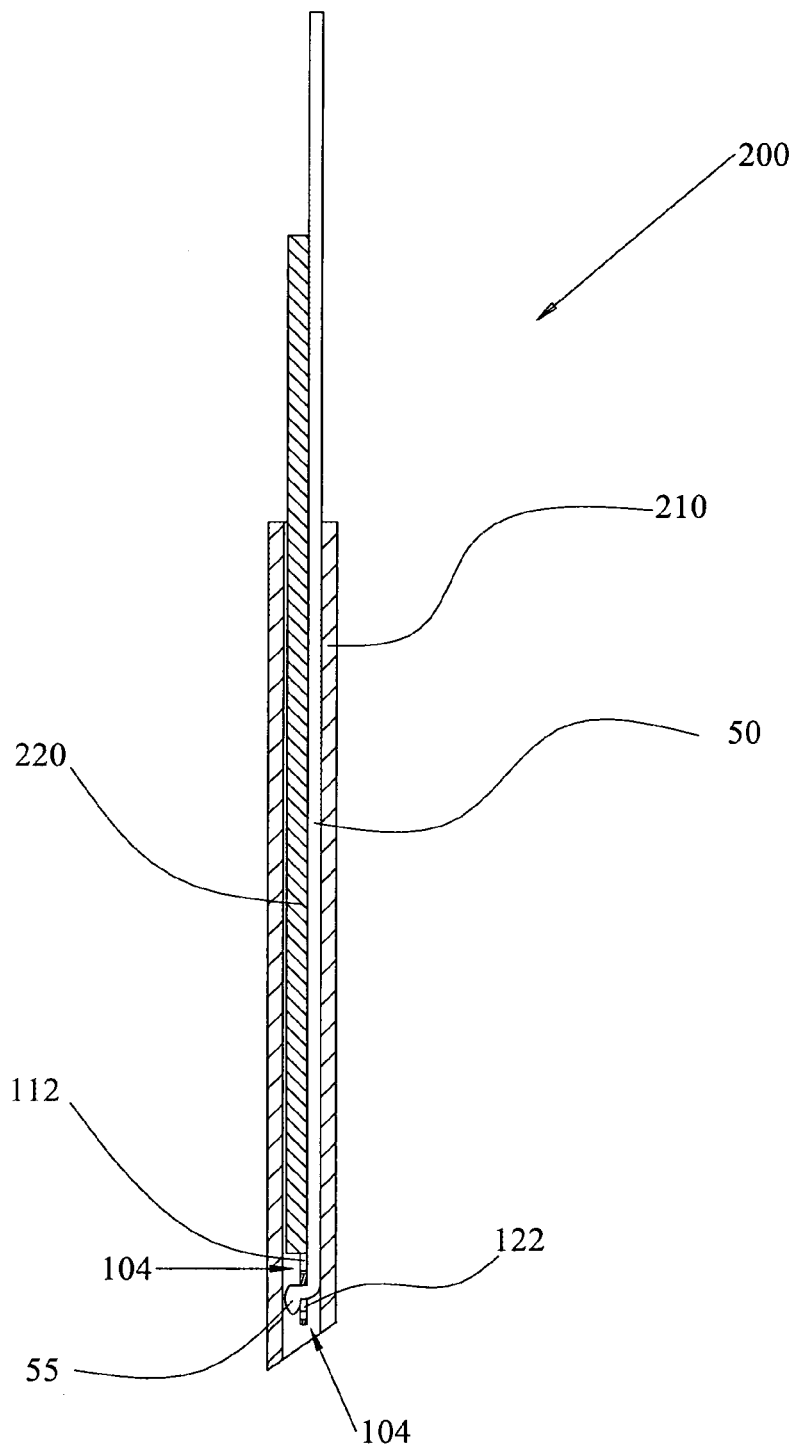
FIG. 16 shows a cut-off, cross-sectional view of a hair implant anchor deployment device for use with hair implant anchors of the present invention.

Reference is now made to FIG. 16 where a cut-off, cross-sectional schematic view of a hair implant anchor deployment device 200 is shown. Device 200 in FIG. 16 is very similar in construction and operation to deployment device 200 in FIGS. 3 and 4. Device 200 in FIG. 16 may be used with anchor 104 shown in FIG. 13 or with anchor 106 of FIG. 14. Hair 50 is inserted into sized opening 122 of anchor 104 with bulbous end 55, the hair bulb, trapped by sized opening 122. When loaded anchor 104 is placed in needle 210, leaves 112 are restrained by needle 210 and are non-extended, the anchor being in its closed configuration. Positioned within needle 210 of deployment device 200 is pusher 220 which is operative to push on leaves 112 of anchor 104 causing anchor 104 to be ejected from device 200. After ejection of anchor 104 into the target tissue, anchor 104 transitions to its open configuration with leaves 112 extending away from the holder of anchor 104 thereby anchoring hair 50 and anchor 104 to the tissue. Pusher 220 may be a rod but may alternatively have an incomplete tubular construction—a tube partially cut away in the longitudinal direction of the tube—similar to the pusher in FIGS. 3 and 4. In fact, the pusher can have any kind of elongated stem that is insertable into the needle's tubular stem. It should be readily evident to one skilled in the art that anchor 106 of FIG. 14 can also employ the deployment device shown in FIG. 16.

The anchors shown and discussed in conjunction with FIG. 12 through FIG. 15 are operatively similar to anchor 100 of FIGS. 1 and 2. In the closed first configuration, the one or more leaves are constrained within or by the deployment device in a position generally parallel to the insertion axis. In the open second configuration, anchors 102, 104, 106 and 108 of FIGS. 12, 13, 14, and 15, respectively, the one or more leaves of the anchors extend away from the insertion axis. The projection of the anchors in their open second configuration on a plane perpendicular to the insertion axis, extends beyond the projection of the anchors on the plane when the anchors are in their closed first configuration.

In FIG. 16, as in FIGS. 3 and 4, the needle and the pusher, forming the anchor deployment device, have a linear construction. It should readily be understood by persons skilled in the art that the needle and pusher forming the deployment device may have a curved construction. Such a construction can be operative to implant hair implant anchors in substantially the same manner as the linear deployment devices discussed herein above in conjunction with FIGS. 3, 4 and 16.

The hair implant anchors and method of implanting the anchors described herein above may be used with hair obtained from the patient or another hair donor. This feature can be utilized advantageously in cases where the patient lacks hair for donation or when changing the patient's hair characteristics are desired. These characteristics include hair color, curliness, etc. . . . . .

Hair with natural, artificial or enhanced natural hair bulbs can be used. An artificial or enhanced natural hair bulb can be formed using medical silicon or other medical adhesives or by using thermal heating techniques. This ability to use hairs with artificial hair bulbs or enhanced natural hair bulbs allows use of several pieces of hair cut from a single long hair strand and allows use of natural hair where the natural hair bulb has been damaged or does not exist. As the anchors of the present invention rely upon geometrical principles, an artificial protrusion on an end of a hair, formed, for example, from a biocompatible material such as silicone adhesive, may be used to replace and function much as a natural hair bulb.

Hair implant anchor 100 may be produced in the following manner. A nitinol tube may first be cut, typically using a laser cutting machine. The leaves 110 of anchor 100 are then shaped to their extended open shape by using one of several conventional nitinol heat treatment processes known to those skilled in the art. This may include placing anchor 100 into an oven after locking it inside a shaping mold. If desired, the surfaces of anchor 100 may be smoothed using any conventional nitinol electro-polishing technique or other chemical or mechanical processes known to those skilled in the art.

When manufacturing alternative anchors 104, 106 or 108 which are cut from a nitinol plate, the above heat treatment process may be spared.

In one embodiment of the present invention, anchor 100 may be coated with an antibacterial agent, e.g. roxithromycin, to prevent potential infections. Alternatively, the anchor may be coated with a copper-based coating, copper having known antimicrobial properties.

In some embodiments of the present invention, the anchor may be made of a biodegradable material which degrades after the hair is well anchored in the fibrous tissue which has grown around the implanted hair. In other embodiments, the anchor may be of a composite construction wherein only some of the anchor is biodegradable degrading after the implanted hair is well anchored in the returning fibrous tissue. In this latter case, there may still be a portion of the anchor that mechanically assists in anchoring the hair to the target tissue. Biodegradable materials which may be used, but are not limited to, are polylactic acid (PLA), polyglycolic acid (PGA), and magnesium alloys.

Advantages of the hair implant anchors, hair implant anchor deployment devices, and multi-hair implantation systems of the present invention are:

1. Rapid implantation of relatively large numbers of hairs;
2. Multiple simultaneous implants are possible requiring fewer sessions and resulting in quicker treatment;
3. Anchoring is more secure;
4. Natural and synthetic hair can be used;
5. Time zero fixation of the implanted hair is possible;
6. Little scarring occurs because hair donation is not required;
7. Hair density and geometrical distribution of the hair can be varied according to the needs of the patient;
8. Angle of implantation can be controlled;
9. Uniformity in implantation depth can be attained;
10. Maximum implantation depth can be controlled and accidental over-penetration can be prevented;
11. There is reduced trauma to the patient because big knots are not required for hair fixation;
12. Suitable for hair implants in eyebrows; and
13. Immediate aesthetic results unlike more conventional hair transplant procedures.

Figure 17B:
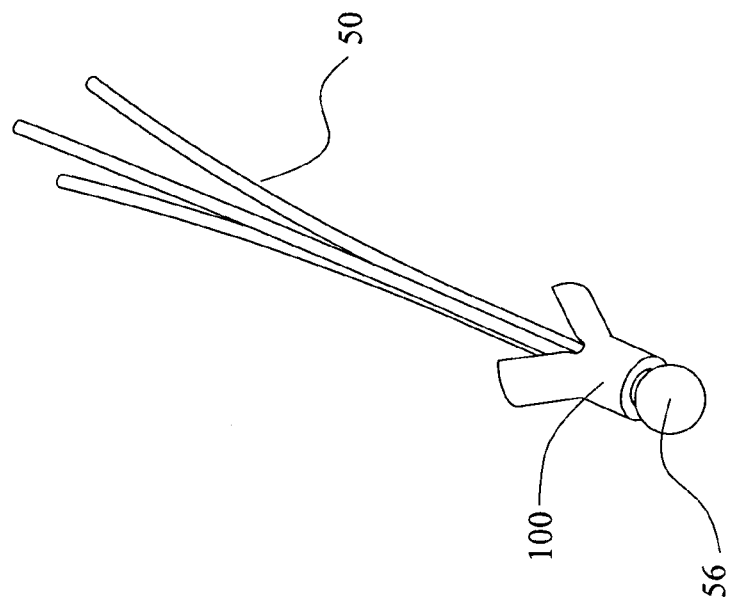
FIGS. 17A and 17B show two different embodiments where a plurality of hairs in a single hair implant anchor may be used.
Figure 17A:
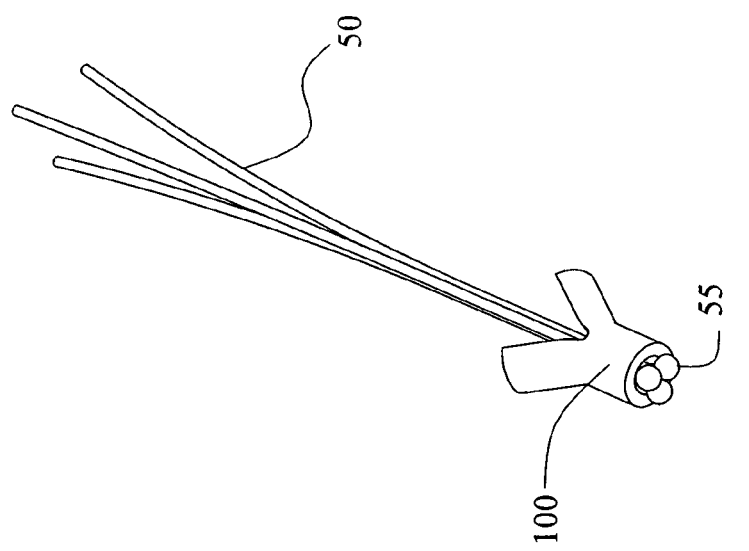

It should be noted that the discussion herein and the accompanying Figures up until now present the anchors, assemblies, devices, systems, and method of the present invention when one hair is held by an anchor. It should readily be understood and as indicated in FIGS. 17A and 17B, to which reference is now made, that the anchors, assemblies, devices systems and method described herein may be used when a plurality of hairs are held by a single anchor. In FIG. 17A, each of the three hairs in the anchor has its own individual hair bulb, natural or artificial; in FIG. 17B the three hairs have a single artificial hair bulb servicing the three hairs in the anchor.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. In addition, citation or identification of any reference in this application shall not be construed as an admission that such reference is available as prior art to the present invention.

It will be appreciated by persons skilled in the art that the present invention is not limited by the drawings and description hereinabove presented. Rather, the invention is defined solely by the claims that follow.

The invention claimed is:

1. A hair implantation device, comprising:
a synthetic hair strand configured for implantation in at least one of eyebrow or scalp target tissue to simulate a human hair and to extend through the target tissue to a location external to a subject individual, the hair strand including a shaft having a first dimension;
a distal end on the hair strand, the distal end of the hair strand having a second dimension greater than the first dimension of the shaft, and constituting a widening of the hair strand in a bulbous shape;
a holder formed of a metal or a metal alloy configured for implantation in the at least one of eyebrow or scalp target tissue, the holder including a tube having a distal end, a proximal end, and a longitudinal axis, and having an opening therethrough sized smaller than the second dimension for retaining the distal end of the hair strand;
at least one resilient metal or metal alloy deployable leaf operatively connected to the holder, wherein the holder and the at least one deployable leaf are configured to be contained within a tubular needle having a longitudinal axis, with the at least one deployable leaf constrained within the needle in a non-deployed state, and to project away from the longitudinal axis of the needle upon exiting the needle in a deployed state to thereby secure the hair strand to the at least one eyebrow or scalp target tissue; and wherein the holder and the at least one deployable leaf constitute an anchor, and wherein the anchor is sized to be implanted fully contained within the scalp or eyebrow target tissue with a longitudinal axis of the anchor transverse to the external surface of the scalp or eyebrow target tissue.

2. The hair implantation device of claim 1, wherein the holder has an outer diameter of between about 0.15 mm to 0.3 mm and is constructed and configured to enable the hair implantation device to be implanted subcutaneously while the hair strand maintains a substantially normative anatomy.

3. The hair implantation device of claim 1, further comprising a plurality of hair strands each having an associated holder, and a plurality of needles, wherein each of the plurality of needles is loaded with a holder, at least one leaf, and a hair strand, and wherein the hair implantation device further comprises a plurality of co-actuatable pushers, each pusher being associated with one of the plurality of needles and being configured to implant each holder, at least one leaf, and hair strand from each of the plurality of needles, substantially simultaneously, and wherein the tube of each holder and associated needle are configured such that in the deployed state, longitudinal axes of each tube generally extend in a direction of needle implantation.

4. The hair implantation device of claim 3, wherein each holder retains only a single hair strand, and wherein portions of the plurality of hair strands extend through proximal ends of the plurality of needles, the extending portions of the plurality of hair strands and the proximal needle ends being configured to remain external to the subject individual when distal ends of the plurality of needles are subcutaneously disposed.

5. The hair implantation device of claim 4, wherein the plurality of needles includes 36 needles each retaining only a single hair strand in a single anchor, and the plurality of pushers includes 36 pushers, and wherein the 36 pushers are configured for simultaneous actuation.

6. The hair implantation device of claim 5, wherein each of the pushers includes an opening extending therethrough, and only a single hair strand extends through the opening of each pusher.

7. The hair implantation device of claim 1, wherein the distal end of the hair strand includes a protrusion forming the bulbous shape.

8. The hair implantation device of claim 7, wherein the protrusion is formed by heating of the shaft of the hair strand.

9. The hair implantation device of claim 8, where the protrusion is a bulb formed by heating of the shaft of the hair strand.

10. The hair implantation device of claim 8, wherein the protrusion is sized to fit within the needle.

11. The hair implantation device of claim 1, wherein the holder and the at least one deployable leaf are integrally formed.

12. The hair implantation device of claim 1, wherein the at least one deployable leaf includes a pair of resilient metal leaves, the pair being integrally formed with the holder.

13. The hair implantation device of claim 1, wherein the target tissue is scalp tissue and wherein the holder and the at least one deployable leaf are sized for implantation in scalp tissue.

14. The hair implantation device of claim 1, wherein the holder is substantially cylindrical having a side wall continuous in directions parallel to and transverse to the longitudinal axis of the holder from the distal end of the holder to a point where the at least one deployable leaf is connected to or formed integrally with the holder.

15. The hair implantation device of claim 1, wherein the holder and the at least one deployable leaf are constructed of nitinol.

16. The hair implantation device of claim 1, wherein the holder and the at least one deployable leaf are cut from a tube by a laser.

17. The hair implantation device of claim 1, wherein the at least one deployable leaf is made of a shape memory alloy and is configured to automatically spring away from the longitudinal axis of the needle when deployed from the needle.

18. The hair implantation device of claim 1, wherein the hair strand is a synthetic polymer.

19. The hair implantation device according to claim 1, wherein the holder is configured such that upon implantation in the target tissue, the hair strand extends from the distal end of the tube to the proximal end of the tube.

20. The hair implantation device according to claim 19, wherein the hair strand is maintained by the holder along the longitudinal axis of the tube.

21. A hair implantation device, comprising:
a hair implant delivery device comprising a needle with a tubular stem and having a longitudinal axis, and a pusher with a tubular stem, the pusher tubular stem positioned within, and substantially concentrically with, the needle tubular stem;
a synthetic hair strand having a shaft with a first dimension, a distal end, and a proximal end, the distal end of the hair strand having a second dimension greater than the first dimension of the shaft, and constituting a widening of the hair strand in a bulbous shape, and wherein the distal end of the hair strand includes a protrusion forming the bulbous shape formed by heating of the shaft of the hair strand;
a hair implant anchor, comprising a cylindrical holder having a continuous side wall throughout the full length of the holder, and having an opening therethrough, a distal end, a proximal end, and at least one resilient deployable leaf operatively connected to the holder, the hair strand positioned in the holder such that the distal end of the hair strand is restrained by the holder,
wherein the anchor has a closed configuration when positioned within the needle with the at least one deployable leaf being constrained in the needle, and an open configuration when the anchor is pushed out of the needle by the pusher into at least one of eyebrow or scalp target tissue, and wherein the at least one deployable leaf is configured to move away from the longitudinal axis of the needle in the open configuration,
wherein the hair anchor is configured so that the hair strand is held by the holder upon exit from the needle; and wherein the anchor is sized to be implanted fully contained within the scalp or eyebrow target tissue with a longitudinal axis of the anchor transverse to the external surface of the scalp or eyebrow target tissue.

22. The hair implantation device according to claim 21 wherein the holder and the at least one deployable leaf are constructed of nitinol.

23. The hair implantation device of claim 21, wherein the holder and the at least one deployable leaf are cut from a tube with a laser.

24. The hair implantation device according to claim 21, wherein the at least one deployable leaf is made of a shape-memory alloy and is configured to spring away from the longitudinal axis of the needle when deployed from the needle.

25. The hair implantation device of claim 21, wherein the hair strand is a synthetic polymer.

26. The hair implantation device according to claim 21, wherein the anchor further comprises a side wall continuous in directions parallel to and transverse to the longitudinal axis of the anchor from the distal end of the holder to a point where the at least one deployable leaf is connected to or formed with the holder.

* * * * *